(12) United States Patent
Cho et al.

(10) Patent No.: US 9,134,211 B2
(45) Date of Patent: Sep. 15, 2015

(54) SURFACE SHAPE MEASURING DEVICE

(71) Applicant: Korea Advanced Institute of Science and Technology, Daejeon (KR)

(72) Inventors: Young-Ho Cho, Daejeon (KR); Jae-Min Kim, Seoul (KR); Dae-Geon Seo, Daegu (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 216 days.

(21) Appl. No.: 13/852,806

(22) Filed: Mar. 28, 2013

(65) Prior Publication Data

US 2013/0255396 A1 Oct. 3, 2013

(30) Foreign Application Priority Data

Mar. 30, 2012 (KR) .................. 10-2012-0033105

(51) Int. Cl.
| | |
|---|---|
| G01B 7/24 | (2006.01) |
| G01N 3/08 | (2006.01) |
| G01B 7/16 | (2006.01) |
| G01L 1/00 | (2006.01) |
| A61B 5/053 | (2006.01) |

(52) U.S. Cl.
CPC .......... *G01N 3/08* (2013.01); *A61B 5/053* (2013.01); *A61B 5/0531* (2013.01); *G01B 7/18* (2013.01); *G01B 7/22* (2013.01); *G01L 1/00* (2013.01)

(58) Field of Classification Search
CPC ............................................. G01B 7/22
USPC ............................................. 73/780
See application file for complete search history.

(56) References Cited

U.S. PATENT DOCUMENTS

| | | | | |
|---|---|---|---|---|
| 4,030,347 | A * | 6/1977 | Norris et al. ................. | 73/769 |
| 6,532,824 | B1 * | 3/2003 | Ueno et al. ................... | 73/780 |
| 7,578,195 | B2 * | 8/2009 | DeAngelis et al. ............ | 73/718 |
| 7,954,385 | B2 * | 6/2011 | Raisanen ...................... | 73/780 |
| 8,104,358 | B1 * | 1/2012 | Jia et al. ....................... | 73/780 |
| 2007/0034013 | A1 * | 2/2007 | Moon et al. ................... | 73/780 |
| 2008/0202251 | A1 * | 8/2008 | Serban et al. ................. | 73/780 |
| 2009/0158856 | A1 * | 6/2009 | Harish et al. ................. | 73/780 |
| 2009/0188325 | A1 * | 7/2009 | Aebersold et al. ............ | 73/780 |
| 2009/0249885 | A1 * | 10/2009 | Shkel et al. ................... | 73/780 |
| 2011/0107842 | A1 * | 5/2011 | Dargahi et al. ............... | 73/780 |
| 2011/0314924 | A1 * | 12/2011 | Chandrasekharan et al. .. | 73/780 |
| 2012/0055257 | A1 * | 3/2012 | Shaw-Klein .................. | 73/780 |

FOREIGN PATENT DOCUMENTS

| | | | |
|---|---|---|---|
| JP | 2005-030840 | A | 2/2005 |
| JP | 2006-515463 | A | 5/2006 |
| JP | 2007-316053 | A | 12/2007 |
| JP | 2008-164557 | A | 7/2008 |

OTHER PUBLICATIONS

Benedek, Mathias et al. "Objective and continuous measurement of piloerection." *Psychophysiology* 47 (2010): 989-993.
Benedek, Mathias and Christian Kaernbach. "Physiological correlates and emotional specificity of human piloerection." *Biological Psychology* 86 (2011): 320-329.
Korean Office Action dated Jun. 24, 2014 issued in corresponding Korean Application No. 10-2012-0033105.

\* cited by examiner

*Primary Examiner* — Christopher Fulton
(74) *Attorney, Agent, or Firm* — Harness, Dickey & Pierce, P.L.C.

(57) ABSTRACT

A surface shape measuring device includes a substrate, an electrode portion including at least one electrode pattern, the electrode pattern extending on the substrate, a coating layer on the substrate to cover the electrode pattern, and a detector electrically connected to the electrode pattern and detecting a change in a physical quantity of the electrode pattern generated by the deformation of the substrate or the coating layer by an external load applied thereto.

11 Claims, 5 Drawing Sheets

SURFACE SHAPE MEASURING DEVICE

CLAIM OF PRIORITY

This application claims priority under 35 USC §119 to Korean Patent Application No. 2012-0033105, filed on Mar. 30, 2011 in the Korean Intellectual Property Office (KIPO), the contents of which are herein incorporated by reference in their entirety.

BACKGROUND

1. Field

Example embodiments relate to a surface shape measuring device. More particularly, example embodiments relate to a surface shape measuring device capable of being attached to a contact surface of subject to measure a load applied thereto.

2. Description of the Related Art

Recognizing quantitative information about an intention or state of a human being through a skin has been one of the major concerns of doctors, psychologists or cognitive scientists for a long time. In electroencephalography (EEG), electrocardiography (ECG), electromyography (EMG) systems, electric signals on the skin surface may be measured to understand the intention or state of a human being. However, in these systems, undesired signals from deep regions below the skin may be detected together with the electrical signals on the skin. Accordingly, there is a need for an indicator using a skin surface itself as a signal source and representing an intention or state of a human being.

Recently, an efficient method for the objective and continuous measurement of piloerection based on an optical recording device is disclosed in the articles by M. Benedek, "Objective and continuous measurement of piloerection", Psychophysiology, Vol. 47, pp. 989-993, 2010, and "Physiological correlates and emotional specificity of human piloerection), Biological Psychology, Vol. 86, pp 320-329, 2011. However, these measuring devices are big and heavy, require an additional fixing means and have limits to a measuring area. Further, stimuli due to an additionally attached sensor may be applied to a measuring area, so it may be difficult to distinguish whether detected reaction of subject is due to the stimulating source or the additional sensor.

SUMMARY

Example embodiments provide device capable of being easily attached on a skin surface of subject without a fixing tool to precisely measure a minute surface change in the skin.

According to example embodiments, there is provided a surface shape measuring device. The device includes a substrate, an electrode portion including at least one electrode pattern, the electrode pattern extending on the substrate, a coating layer on the substrate to cover the electrode pattern, and a detector electrically connected to the electrode pattern and detecting a change in a physical quantity of the electrode pattern generated by the deformation of the substrate or the coating layer by an external load applied thereto.

In example embodiments, the electrode portion may include a first electrode pattern and a second electrode pattern spaced apart from each other.

In example embodiments, the detector may detect capacitance between the first electrode pattern and the second electrode pattern.

In example embodiments, the first and second electrode patterns may extend in a spiral.

In example embodiments, the spacing distance between the first and second electrode patterns may remain constant as each of the first and second patterns revolves around the central point.

In example embodiments, the spacing distance between the first and second electrode patterns may be changed as each of the first and second electrode patterns revolves around the central point.

In example embodiments, the electrode pattern may extend in a serpentine shape.

In example embodiments, the detector may detect a resistance of the electrode pattern.

In example embodiments, the electrode portion may include a plurality of the electrode patterns arranged in a matrix shape.

In example embodiments, the substrate or the coating layer may further include a protrusion on a surface thereof to contact with a surface of an object.

In example embodiments, the device may further include a calculator connected to the detector to calculate a variation in a surface shape based on the detected change in the physical quantity According to example embodiments, the surface shape measuring device may have a simple structure of a single-layered electrode portion surrounded by the substrate and the coating layer. Accordingly, the surface shape measuring device may be manufactured by a single mask process without additional alignment processes, to thereby reduce the manufacturing cost. Further, the surface shape measuring device may precisely measure a minute surface change in a skin to be used to understand the state or intention of a human being.

BRIEF DESCRIPTION OF THE DRAWINGS

Example embodiments will be more clearly understood from the following detailed description taken in conjunction with the accompanying drawings. FIGS. 1 to 7 represent non-limiting, example embodiments as described herein.

FIG. 1 is a plan view illustrating a surface shape measuring device in accordance with example embodiments.

FIG. 2 is a cross-sectional view taken along the II-IF line in FIG. 1.

FIG. 3 is a perspective view illustrating a deformation of the substrate in FIG. 1.

FIG. 6 is a plan view illustrating a surface shape measuring device in accordance with example embodiments.

FIG. 7 is a perspective view illustrating a surface shape measuring device in accordance with example embodiments.

DESCRIPTION OF EMBODIMENTS

Figure 1:
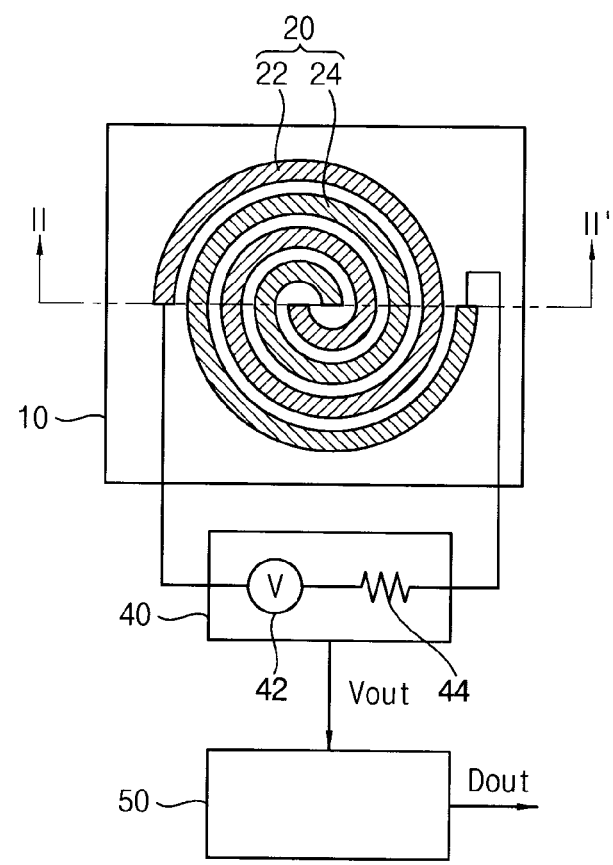

Various example embodiments will be described more fully hereinafter with reference to the accompanying drawings, in which some example embodiments are shown. The present inventive concept may, however, be embodied in many different forms and should not be construed as limited to the example embodiments set forth herein. Rather, these example embodiments are provided so that this description will be thorough and complete, and will fully convey the scope of the present inventive concept to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third, fourth etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present inventive concept.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present inventive concept. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present inventive concept.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 2:
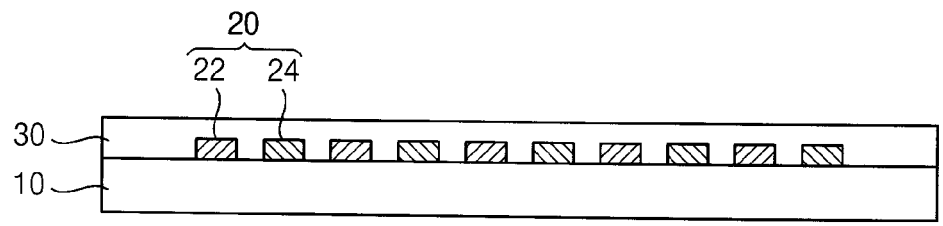
Figure 3:
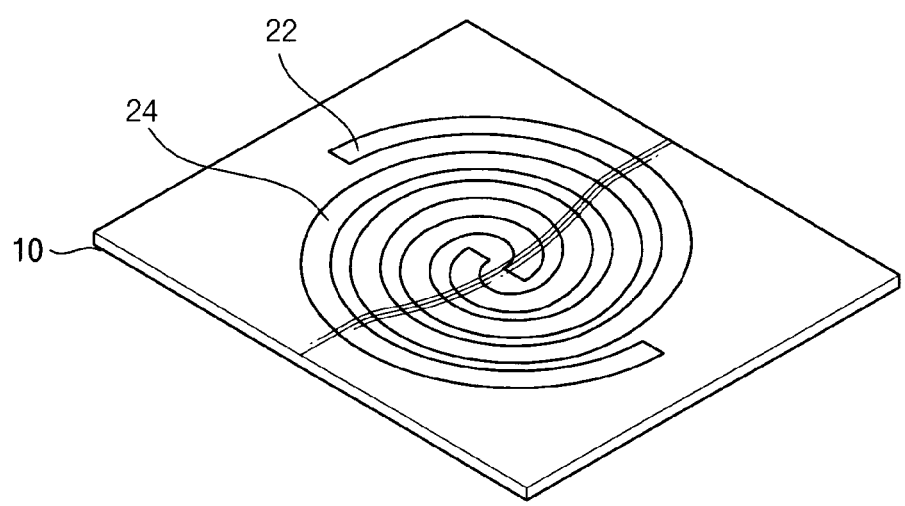

FIG. 1 is a plan view illustrating a surface shape measuring device in accordance with example embodiments. FIG. 2 is a cross-sectional view taken along the II-IF line in FIG. 1. FIG. 3 is a perspective view illustrating a deformation of the substrate in FIG. 1.

Referring to FIGS. 1 to 3, a surface shape measuring device may include a substrate 10, an electrode portion 20 on the substrate 10, a coating layer 30 covering the electrode portion 20, a detector 40 electrically connected to the electrode portion 20, and a calculator 50 connected to the detector 40.

The substrate 10 may include a flexible material deformable by contact with an external object. For example, the substrate 10 may include a flexible polymer material.

In example embodiments, the electrode portion 20 may include at least one electrode pattern extending on the substrate 10. The electrode portion 20 may include a first electrode pattern 22 and a second electrode pattern 24 that extend on the substrate 10 respectively. The first electrode pattern 22 and the second electrode pattern 24 may be spaced apart from each other. The first and second electrode patterns 22, 24 may extend in a spiral on a plane on the substrate 10.

For example, the electrode pattern may include a conductive polymer material or a metal having a thin thickness. The electrode pattern may have a multi-layered structure of a conductive polymer and a metal layer. The metal layer may be formed by a plating process, a deposition process, a sputtering process, etc.

The coating layer 30 may be formed on the substrate 10 to cover the first and second electrode patterns 22, 24. The coating layer 30 may include a flexible material deformable by contact with an external object. For example, the coating layer 30 may include a flexible polymer material.

The detector 40 may be electrically connected to the electrode portion 20, to detect a physical quantity of the electrode pattern that is changed in proportion to the deformation of the substrate 10 or the coating layer 30 by the external pressure applied thereto.

In example embodiments, the detector 40 may be electrically connected to the first electrode pattern 22 and the second electrode pattern 24. The detector 40 may include a power source 42 and a detecting portion 44. Accordingly, the detector 40 may detect a capacitance between the first electrode pattern 22 and the second electrode pattern 24.

As illustrated in FIG. 3, when a pressure is applied to any one of the substrate 10 and the coating layer 30, the relative position of the first and second electrode patterns 22, 24 is changed, and thus, the electrical capacitance between the first and second electrode patterns 22, 24 is charged accordingly.

As an external force is applied to the substrate 10 or the coating layer 30, the first and second electrode patterns 22, 24 may be deformed so that a capacitance between the first and second electrode patterns 22, 24 is changed, and the detector 40 may detect the variation in the capacitance. That is, the change in the physical quantity, that is, the electrical capacitance, generated by the change of the relative position between the first and second electrode patterns 22, 24 may be detected to thereby provide information about the external force.

The capacitance of a parallel-plate capacitor constructed of two parallel plates is known to be approximately equal to the following Equation 1. In here, $\varepsilon_r$ is the dielectric constant of the dielectric material between the plates, $\varepsilon_0$ is the vacuum permittivity, A is the area of overlap of the two plates, and d is the distance between the separate plates.

$$C = \varepsilon_0 \varepsilon_r \frac{A}{d} \qquad \text{Equation 1}$$

As an external force is applied, the first electrode pattern 22 and the second electrode pattern 24 may be deformed in a direction of the applied external force to be spaced apart more from each other. Accordingly, the distance d may be increased and the capacitance C may be decreased. For example, when the power source 42 of the detector 40 applies a voltage to the electrode portion 20, a change in a voltage across a resistance, that is, the detecting portion 44 that is electrically connected to the electrode portion 20, may be detected to obtain the change in the capacitance.

The calculator 50 may calculate and determine a variation in a surface shape based on the change in the physical quantity detected by the detector 40.

Although an identical pressure or force is applied to the device, the deformation of the device may vary according to materials or thicknesses of the substrate 10, the coating layer 30 and the electrode pattern, to have an effect on the sensitivity of the change in the capacitance and the detectable range of the surface shape. Accordingly, the materials and thicknesses of the substrate 10, the coating layer 30 and the electrode pattern may be selected for desired applications, to determine the sensitivity of the change in the capacitance and the detectable range of the surface shape. A Young's modulus is the mathematical description of a substance's tendency to be deformed when a force is applied thereto. For example, when the Young's modulus of the substrate 10, the coating layer 30 and the electrode pattern is relatively small, the device may be easily deformed even by a relatively small pressure or force, to provide a sensor capable of measuring a surface shape of an object under a relatively small pressure or force.

In addition, the materials and thicknesses of the substrate 10, the coating layer 30 and the electrode pattern may be related to a tight contact with a surface of an object as well as the deformability of the device. In order for a device to be stuck closely to a deformable surface such as a skin, it may be preferable that the thicknesses of the substrate 10, the coating layer 30 and the electrode pattern are relatively small to decrease a flexural strength.

The flexural strength of the device may be represented by the following Equation 2. In here, EIdevice is the flexural strength of the total device, EIelectrode is the flexural strength of the electrode pattern, EIsubstrate is the flexural strength of the substrate 10 and the coating layer 30, and $\alpha$ is an area ratio of the electrode portion 20 occupying the total device.

$$EI_{device} = \alpha EI_{electrode} + (1-\alpha) EI_{substrate} \qquad \text{Equation 2}$$

In this case, EIelectrode may be represented by the following Equation 3. In here, E1 is the Young's modulus of the substrate 10, E2 is the Young's modulus of the electrode pattern, E3 is the Young's modulus of the coating layer 30, h1 is the thickness of the substrate 10, h2 is the thickness of the electrode pattern, h3 is the thickness of the coating layer 30, and b is represented by the following Equation 4.

$$EI_{electrode} = \sum_{i=1}^{3} E_i h_i \left[ \left(b - \sum_{j=1}^{i} h_j\right)^2 + \left(b - \sum_{j=1}^{i} h_j\right) h_j + \frac{1}{3} h_i^2 \right] \qquad \text{Equation 3}$$

$$b = \sum_{i=1}^{3} E_i h_i \left( \sum_{j=1}^{i} h_j - \frac{1}{2} h_i \right) \Big/ \sum_{i=1}^{3} E_i h_i \qquad \text{Equation 4}$$

In addition, EI substrate may be represented by the following Equation 5. In here, Esubstrate is the Young's modulus when the substrate 10 and the coating layer 30 include the same material, and h is the thickness of the total device.

$$EI_{substrate} = \frac{E_{substrate} h^3}{12} \qquad \text{Equation 5}$$

When the device is stuck completely to a surface of an object, the following Equation 6 may be established. In here, Esurface is the Young's modulus of the object having the contact surface to be measured, hrough is the maximum stickable amplitude when the roughness of the contact surface is modeled as a trigonometrical function, $\lambda$rough is the wavelength of the surface roughness, EIdevice is the flexural strength of the total device, and $\gamma$ is the effective sticking work between the device surface and the contact surface of the object.

$$\frac{E_{surface} h_{rough}^2}{\gamma \lambda_{rough}} < 16 + \frac{E_{surface} \lambda_{rough}^3}{\pi^3 EI_{device}} \qquad \text{Equation 6}$$

Accordingly, in order to stick completely the entire device to the contact surface, it may be preferable that the materials and thicknesses of the substrate 10, the coating layer 30 and the electrode pattern may be selected such that the roughness is greater than the real roughness of the contact surface.

Referring to Equations 1 to 6, the lower the flexural strengths of the substrate 10, the coating layer 30 and the electrode portion are, the more closely the entire device is stuck to a surface having a relatively low Young's modulus, such as a skin surface of a human being.

As mentioned above, the surface measuring device may be stuck closely to a surface to be measured without a fixing tool such as an adhesive, a band, etc, to measure a load applied to the sensing device using the change in the surface shape.

Figure 4A:
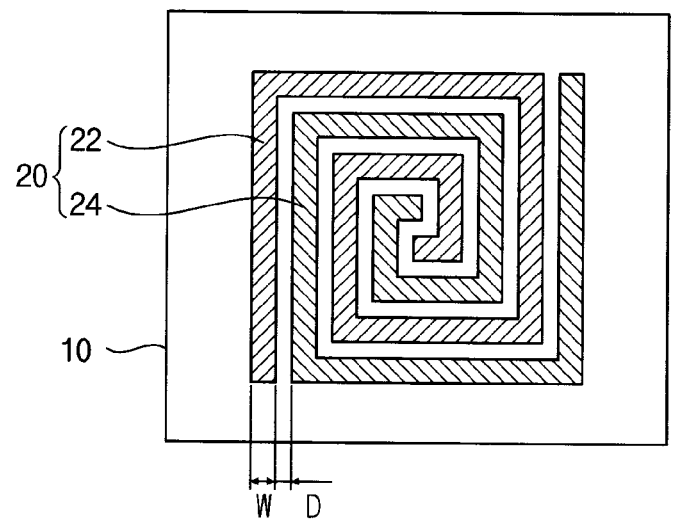
FIGS. 4A and 4B are plan views illustrating various shapes of the electrode patterns.
Figure 4B:
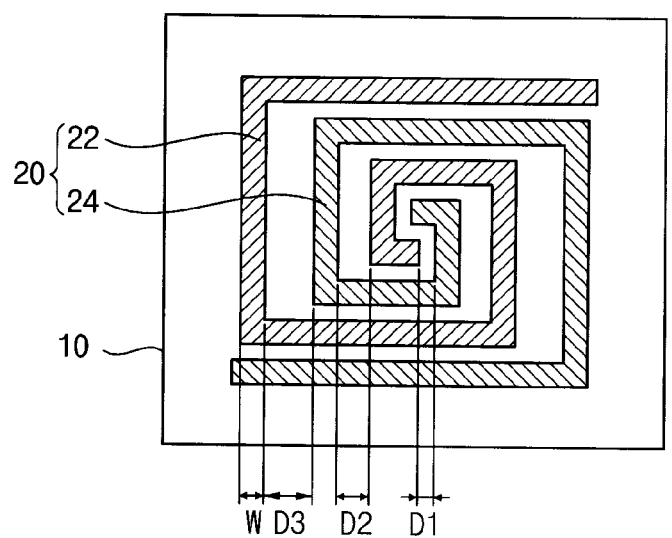

FIGS. 4A and 4B are plan views illustrating various shapes of the electrode patterns.

Referring to FIGS. 4A and 4B, the width (W) or the spacing distance (D) between the first and second electrode patterns 22, 24 may remain constant or may be decreased or increased from the central point as each of the patterns revolves around the central point. As illustrated in FIG. 4B, the spacing distances (D1, D2, D3) between the first and second electrode patterns 22, 24 may be increased from the central point as the curves revolve around the central point.

The width and the spacing distance between the first and second electrode patterns 22, 24 may be selected to control the deformability of the device as well as the capacitance and the sensitivity of the change in the capacitance.

For example, when the widths of the first and second electrode patterns 22, 24 are increased, the flexural strength of the device may be increased to reduce the deformibilty thereof so that the device is not easily deformed by a pressure or force, and the area of the electrode may be increased so that the capacitance is increased. When the spacing distance between the first and second electrode patterns 22, 24 is increased, the flexural strength of the device may be decreased to increase the deformiblity thereof so that the device is easily deformed by a pressure or force, and the distance between the electrodes may be increased so that the capacitance is decreased.

As illustrated in FIGS. 4A and 4B, the width and the spacing distance between the first and second electrode patterns 22, 24 of the electrode portion 20 may be selected for desired applications to determine the deformability of the device as well as the capacitance and the sensitivity of the change in the capacitance.

Figure 5A:
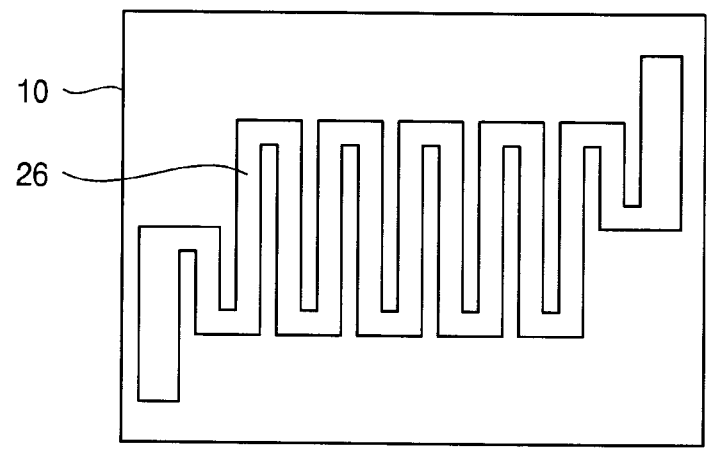
FIGS. 5A and 5B are plan views illustrating a surface shape measuring device in accordance with example embodiments.
Figure 5B:
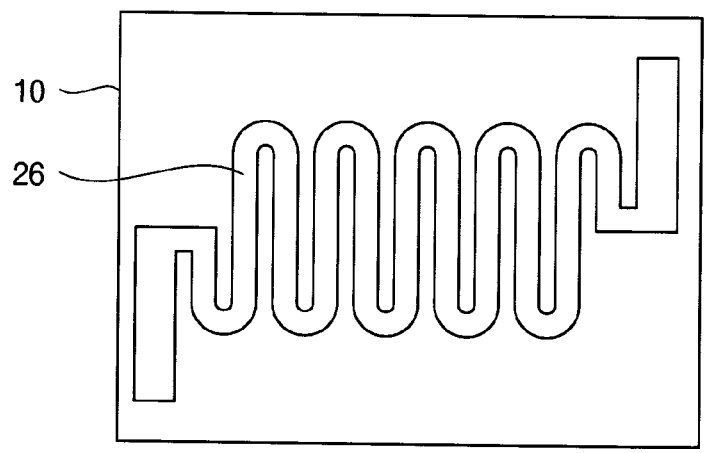

FIGS. 5A and 5B are plan views illustrating a surface shape measuring device in accordance with example embodiments. The present embodiment may be substantially the same as that of FIG. 1 except for the electrode portion. Thus, the same reference numerals will be used to refer to the same or like elements as those described in the Embodiment of FIG. 1 and any further repetitive explanation concerning the above elements will be omitted.

Referring to FIGS. 5A and 5B, an electrode portion of a surface shape measuring device may include an electrode pattern 26 extending in a serpentine shape. In this embodiment, the electrode portion may include a strain gage. As illustrated in FIG. 5A, the strain gage of the electrode portion may have a serpentine shape of mainly straight lines. As illustrated in FIG. 5B, the strain gage of the electrode portion may have a serpentine shape of a combination of straight lines and curved lines. Accordingly, the surface shape measuring device may detect a change in a resistance of the electrode pattern 26 by an external load, to measure a change in a surface shape of an object.

Figure 6:
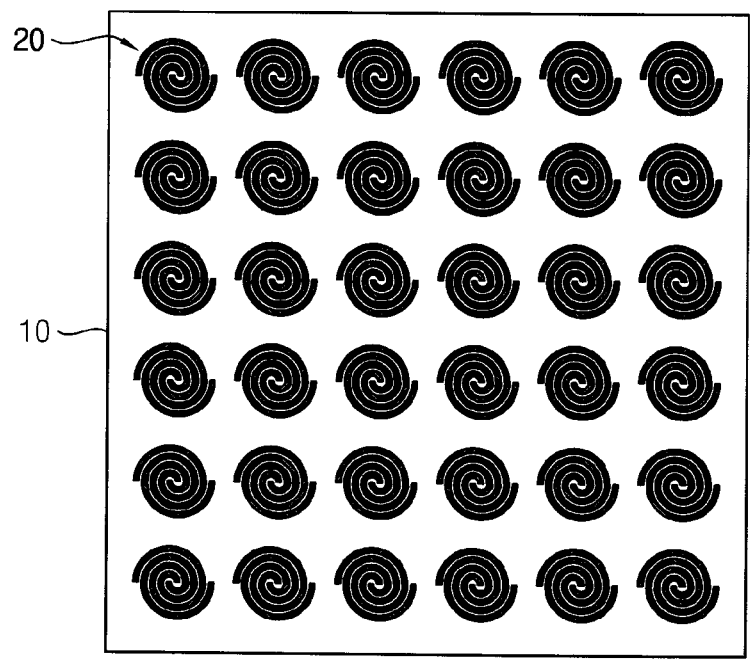

FIG. 6 is a plan view illustrating a surface shape measuring device in accordance with example embodiments. The present embodiment may be substantially the same as that of FIG. 1 except for the electrode portion. Thus, the same reference numerals will be used to refer to the same or like elements as those described in the Embodiment of FIG. 1 and any further repetitive explanation concerning the above elements will be omitted.

Referring to FIG. 6, a surface shape measuring device may include an electrode portion 20 having a plurality of electrode patterns arranged in a matrix shape on a substrate 10. The electrode patterns may be arranged in a matrix shape to measure surface shapes at a plurality of detecting points. At the detecting points, the electrode patterns of the electrode portion 20 may be deformed by external loads to output deformation signals and obtain information about the surface shape at different positions.

Figure 7:
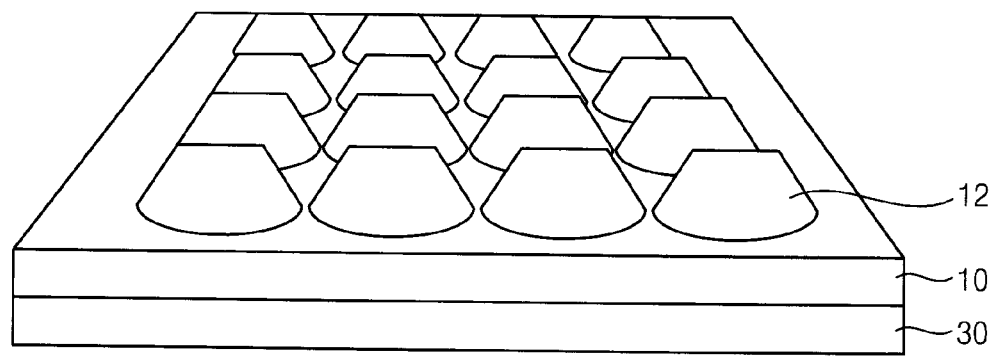

FIG. 7 is a perspective view illustrating a surface shape measuring device in accordance with example embodiments. The present embodiment may be substantially the same as that of FIG. 1 except for the surface of the substrate. Thus, the same reference numerals will be used to refer to the same or like elements as those described in the Embodiment of FIG. 1 and any further repetitive explanation concerning the above elements will be omitted.

Referring to FIG. 7, a substrate 10 or a coating layer 30 of a surface shape measuring device may include a plurality of protrusions 12 on a contact surface of the device. As illustrated in FIG. 7, the coating layer 30 may be formed on a first surface of the substrate 10 and the protrusions 12 may be formed on a second surface of the substrate 10 opposite to the first surface. A deformable surface of an object may be stuck to the second surface of the substrate 10, that is, the contact surface of the device. The protrusions 12 may protrude from the contact surface of the substrate 10. Accordingly, the protrusions 12 on the substrate 10 or the coating layer may effectively transfer the pressure or force to an electrode portion 20, to thereby improve the sensitivity of the surface shape measuring device.

According to example embodiments, the surface shape measuring device may be manufactured using a flexible material to have a relatively small thickness. The surface shape measuring device may be easily attached on a skin surface of subject without a fixing tool and may not cause a physical stimulus to the subject. The surface shape measuring device may be deformed by the change in the surface shape, to precisely measure a minute surface change.

The foregoing is illustrative of example embodiments and is not to be construed as limiting thereof. Although a few example embodiments have been described, those skilled in the art will readily appreciate that many modifications are possible in the example embodiments without materially departing from the novel teachings and advantages of the present inventive concept. Accordingly, all such modifications are intended to be included within the scope of the present inventive concept as defined in the claims. In the claims, means-plus-function clauses are intended to cover the structures described herein as performing the recited function and not only structural equivalents but also equivalent structures. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. A surface shape measuring device, comprising:
    a substrate having a flexible polymer material deformable by contact with an external object;
    an electrode portion including at least one electrode pattern, the electrode pattern extending on the substrate and having a conductive polymer material;
    a coating layer on the substrate to cover the electrode pattern and having a flexible polymer material deformable by contact with the external object; and
    a detector electrically connected to the electrode pattern and configured to detect a change in a physical quantity of the electrode pattern generated by at least one of a deformation of the substrate and the coating layer by the external object applied thereto,
    wherein the substrate or the coating layer has a surface roughness greater than a surface of the external object so that the surface shape measuring device makes a conformal contact with the surface of the external object, and
    the detector is configured to detect the change in the physical quantity of the electrode pattern depending on a shape deformation of the surface of the external object in a state where the substrate or the coating layer is conformally attached to the external object.

2. The device of claim 1, wherein the electrode portion comprises a first electrode pattern and a second electrode pattern spaced apart from each other.

3. The device of claim 2, wherein the detector is configured to detect capacitance between the first electrode pattern and the second electrode pattern.

4. The device of claim 2, wherein the first and second electrode patterns extend in a spiral.

5. The device of claim 4, wherein a spacing distance between the first and second electrode patterns remains constant as each of the first and second electrode patterns revolves around the central point.

6. The device of claim 4, wherein a spacing distance between the first and second electrode patterns is changed as each of the first and second electrode patterns revolves around the central point.

7. The device of claim 1, wherein the electrode pattern extends in a serpentine shape.

8. The device of claim 7, wherein the detector detects a resistance of the electrode pattern.

9. The device of claim 7, wherein the substrate or the coating layer further comprises a protrusion on a surface thereof to contact with the surface of the external object.

10. The device of claim 1, wherein the electrode portion comprises a plurality of electrode patterns arranged in a matrix shape.

11. The device of claim 1, further comprising:
a calculator connected to the detector, the calculator configured to calculate a variation in a surface shape of at least one of the deformation of the substrate and the coating layer based on the detected change in the physical quantity.

* * * * *